United States Patent [19]

Coneski et al.

[11] Patent Number: 5,198,878
[45] Date of Patent: Mar. 30, 1993

[54] SUBSTRATE MACHINING VERIFIER

[75] Inventors: Anthony F. Coneski, Newburgh; Yea-Sen Lin; George B. VanderGheynst, both of LaGrangeville, all of N.Y.

[73] Assignee: International Business Machines Corporation, Armonk, N.Y.

[21] Appl. No.: 621,698

[22] Filed: Nov. 30, 1990

[51] Int. Cl.$^5$ .................. G01B 11/00; H01L 27/14
[52] U.S. Cl. .................................. 356/394; 356/241
[58] Field of Search ............ 356/394, 398, 376, 237, 356/241; 250/553, 565, 213 A, 214 SW; 357/30 H, 30 R, 30 P, 32, 45

[56] References Cited

U.S. PATENT DOCUMENTS

| | | | |
|---|---|---|---|
| 4,425,829 | 1/1984 | Kranik et al. | 83/62.1 |
| 4,448,532 | 5/1984 | Joseph et al. | 356/394 |
| 4,508,453 | 4/1985 | Hara et al. | 356/394 |
| 4,532,650 | 7/1985 | Wihl et al. | 382/8 |
| 4,555,798 | 11/1985 | Broadbent, Jr. et al. | 382/8 |
| 4,559,603 | 12/1985 | Yoshikawa | 356/394 |
| 4,560,273 | 12/1985 | Ando et al. | 356/241 |
| 4,633,504 | 12/1986 | Wihl | 382/54 |
| 4,674,869 | 6/1987 | Pryor et al. | 356/394 |
| 4,680,627 | 7/1987 | Sase et al. | 358/101 |
| 4,692,690 | 9/1987 | Hara et al. | 356/394 |
| 4,805,123 | 2/1989 | Specht et al. | 364/559 |
| 4,877,326 | 10/1989 | Chadwick et al. | 356/394 |
| 4,891,682 | 1/1990 | Yusa et al. | 357/30 H |
| 4,893,346 | 1/1990 | Bishop | 382/8 |
| 4,930,890 | 6/1990 | Hara et al. | 356/237 |
| 5,015,097 | 5/1991 | Nomoto et al. | 356/394 |

FOREIGN PATENT DOCUMENTS

| | | |
|---|---|---|
| 0111404 | 11/1983 | European Pat. Off. |
| 2500929 | 3/1981 | France |
| 0239042 | 10/1987 | Japan .................. 356/241 |

OTHER PUBLICATIONS

IBM Patent Application, Ser. No. 07/428,686, Filed Oct. 30, 1989, M. J. LaPlante et al., "Formation Of High Quality Patterns For Substrates And Apparatus Therefor."

IBM Technical Disclosure Bulletin, vol. 2, No. 4, pp. 98-100, Dec. 1959, F. J. Droege et al., "Hole Count Verifier."

IBM Technical Disclosure Bulletin, vol. 23, No. 9, pp. 4076-4077, Feb. 1981, D. H. Strope et al., "Optical Inspection System."

*Primary Examiner*—Richard A. Rosenberger
*Assistant Examiner*—Hoa Q. Pham
*Attorney, Agent, or Firm*—Richard Lau; James R. Warnot, Jr.

[57] ABSTRACT

A system for machining and for verifying the machining of substrates includes an energy beam located to impinge upon machined features of the substrates and a photodiode switching circuit matrix for detecting those portions of the energy beam which impinge upon the machined features of the substrate. The photodiode switching circuits include a current boost resistor in parallel with the photodiode which allows greater current to flow through the output diode, thereby increasing its switching speed. Pairs of photodiode circuits of the array are sequentially energized so that dual strings of outputs are produced. These outputs are then multiplexed and digitized. The digital outputs are compared in a verifier controller with a predetermined set of data to determine accuracy of the machining process. Substrates to be machined and verified can be mounted on a single X-Y table so that the machining and verification processes can be accomplished simultaneously.

49 Claims, 3 Drawing Sheets

SUBSTRATE MACHINING VERIFIER

TECHNICAL FIELD

This invention relates to methods and apparatus for machining and for verifying the machining of a workpiece such as an electronic device substrate. More particularly, in a preferred embodiment, this invention relates to methods and apparatus for accurately verifying the machining of features such as holes, using a photodiode array which produces strings of electrical signals which are then converted into multiplexed digital data.

BACKGROUND OF THE INVENTION

As the performance capabilities of electronics and computer systems increase, the semiconductor devices and supporting packaging substrates which make up these systems grow in complexity. Multilayer ceramic (MLC) substrates used in integrated circuit semiconductor package structures may have over 50 individual layers. Each of these layers may have over 50,000 holes and interconnecting patterns and may in some cases contain up to 100,000 holes. Rapid and accurate machining of these holes is necessary for an economical manufacturing process. Current machining devices include the multiple punch apparatus described in Kranik, U.S. Pat. No. 4,425,829. Other substrate machining methods include a laser drilling system such as that described in U.S. patent application Ser. No. 07/428,686, filed Oct. 30, 1989.

It is essential that each of this multiplicity of holes be accurately and completely machined. If a single hole in any layer of the substrate is improperly machined, it may be necessary to scrap the entire substrate. It is therefore necessary to verify the machining operation at the earliest possible point in the manufacturing sequence.

Methods and apparatus exist in the art for verifying the machining of various substrates and for verifying the patterns on substrates such as printed circuit boards, photomasks, or semiconductor wafers. An early system for verifying punch card holes in a card reader is disclosed in Droege, IBM Technical Disclosure Bulletin Vol. 2, No. 4, December 1959, pp. 98-100. Droege discloses a system in which after reading a card at two successive stations the number of holes read at each station is compared.

Other verifying systems operate by comparing two patterns, which should be identical, to detect the presence of inconsistencies between the patterns. The invention of Sase et al., U.S. Pat. No. 4,680,627 generates images of the patterns on two printed circuit boards and compares those images as a means of verification. Verification systems for photomasks typically analyze two portions of the photomask which are designed to be identical to detect any inconsistencies. Such systems are disclosed in Hara et al., U.S. Pat. No. 4,508,453; Specht et al., U.S. Pat. No. 4,805,123; Wihl, U.S. Pat. No. 4,633,504; Wihl et al., U.S. Pat. No. 4,532,650; and Joseph et al., U.S. Pat. No. 4,448,532.

Bishop, U.S. Pat. No. 4,893,346, discloses an optical inspection system which creates a fictitious image of the object to be verified, determines the allowable variations from this fictitious image, and uses these allowable variations in analyzing subsequent objects. Chadwick et al., U.S. Pat. No. 4,877,326 discloses an inspection apparatus which incorporates a quasi-Lambertian illumination device. U.S. patent application Ser. No. 07/428,686, filed Oct. 30, 1989, discloses a verifier which includes a rapidly scanning laser beam, a photocell, and a comparing circuit.

Strope et al., IBM Technical Disclosure Bulletin Vol. 23, No. 9, February 1981, pp. 4076-4077, discloses an optical inspection system which uses a linear array of charge coupled photodiodes. This array produces alternate streams of electrical signals which are then converted to signals which represent either a black or a white level, corresponding to the absence or presence of a hole, respectively.

Broadbent, Jr. et al., U.S. Pat. No. 4,555,798 discloses an optical system for inspecting hole quality which also uses a linear array of equally spaced photodiodes. The photodiodes are on a spacing providing multiple photodiodes for analysis of a single hole as the substrate is stepped in an axis perpendicular to the axis along which the photodiodes are arranged. The photodiodes produce an output corresponding to either a 0 or a 1. The outputs of the photodiodes are then analyzed to generate a hole profile.

Another inspection system utilizing a linear array of photodiodes is disclosed in Sredic, French Patent No. 2,500,925. As in the Broadbent device, Sredic discloses a device in which the photodiode outputs correspond to either a digital 0 or 1. These signals are then transmitted in series and analyzed. In one embodiment the Sredic device can only be used to detect the present or absence of holes. In a second embodiment in which the diode array is denser than the hole spacing the Sredic invention can measure the position and diameter deviations of the holes as well.

SUMMARY OF THE INVENTION

Current verification systems show that a need exists for a machining and verifying system which can manipulate sensor output at a speed suitable for use with high speed machining systems and which can flexibly analyze output which corresponds to a variety of machined feature conditions.

It is therefore an object of the present invention to provide a machining verification system which can generate digital signals from two strings of sensor data and compare these digital signals with stored data.

It is a further object of the invention to provide an apparatus for high speed two-dimensional analysis of a machined substrate.

It is yet a further object of this invention to provide a sensor circuit which can produce output data at a speed suitable for use with high speed machining systems.

It is still a further object of the invention to provide an apparatus which simultaneously machines and verifies the machining.

It is still another object of the present invention to provide a method for verifying workpiece machining at a speed suitable for use with high speed machining methods.

In accordance with these and other objects of the present invention a system for verifying substrate machining is provided which includes means for mounting a substrate and a source of an energy beam located to impinge upon the substrate. The system also contains means for detecting those portions of the energy beam which impinge on machined features of the substrate. The detecting means produce at least two sets of electrical signals. An important aspect of the system is means for converting the electrical signals into at least two strings of digital output data. The system then uses verifier controller means to compare the digital output data with a predetermined set of stored data to verify machining accuracy.

The invention also provides a substrate machining system which includes means for mounting a verifying substrate and a source of electromagnetic energy placed to impinge upon the verifying substrate. An important aspect of the invention is a two-dimensional photodiode switching circuit matrix placed to detect the energy impinging on the machined features of the verifying substrate. Each circuit has an output signal in response to the energy and the matrix has a plurality of outputs. The output signals of the switching circuit are converted into multiplexed digital output data, which is compared with predetermined stored data to verify machining accuracy in verifier controller means.

In a more particular embodiment the switching circuit provides a photodiode circuit having at least one input and one output which includes a photodiode with its anode connected to a voltage source. The circuit also includes an input switching diode with its anode connected to an input of the circuit and its cathode connected to the photodiode cathode. The circuit also includes an output switching diode with its anode connected to an output of the circuit and its cathode connected to both the input diode and the photodiode cathodes. An important aspect of the switching circuit is a current boost resistor in parallel with the photodiode which allows increased current to flow thereby increasing the switching speed of the output switching diode.

The invention also provides a method for verifying substrate machining which includes mounting a substrate to be machined and locating an energy beam for impinging on the machine features of the substrate. An important aspect of the method is detecting portions of the energy beam impinging on machined features of the substrate and producing at least two sets of electrical signals, which are then converted into at least two strings of digital output data. The digital output data is compared with a predetermined set of data to verify accuracy of the machining operation.

The foregoing and other objects, features and advantages of the invention will be apparent from the following more particular description of a preferred embodiment of the invention as illustrated in the accompanying drawings.

BRIEF DESCRIPTION OF THE DRAWINGS

In the accompanying drawings forming a material part of this disclosure.

DETAILED DESCRIPTION OF THE INVENTION

Figure 1:
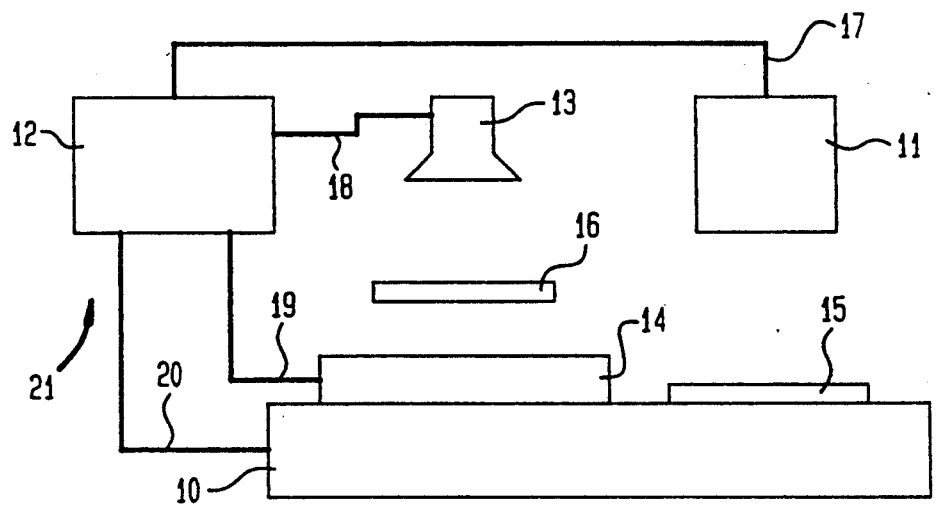
FIG. 1 is a schematic block diagram of the verifying and machining system comprising the present invention.

Referring to the drawings in more detail and particularly referring to FIG. 1 of the invention, there is shown the substrate machining and verifying system 21 according to the present invention. The system 21 includes mounting means 10 for mounting a verifying substrate 16 in a verifying position. In a preferred embodiment mounting means 10 is an X-Y table and includes means for mounting machining substrate 15. In addition to providing a mounting location, X-Y table 10 also includes means for translating both substrates for both the machining and verifying operations. Suitable combinations of devices such as motors, power trains, and slides for achieving this translation are well know to those skilled in the art. An important machining operation and a preferred embodiment of the present invention is machining holes. It should be emphasized that the scope of the present invention encompasses all types of machined features and that the embodiment showing machining and verifying of holes is for purposes of illustration and not of limitation.

The system also includes a source of an energy beam 13 located to impinge upon verifying substrate 16. The energy beam source may comprise any electromagnetic energy source and in a preferred embodiment is a collimated light source such as the light source manufactured by Tamarack Scientific, Part Number PRX12H-766, which produces visible white light and uses a General Electric DDL type lamp.

Figure 4:
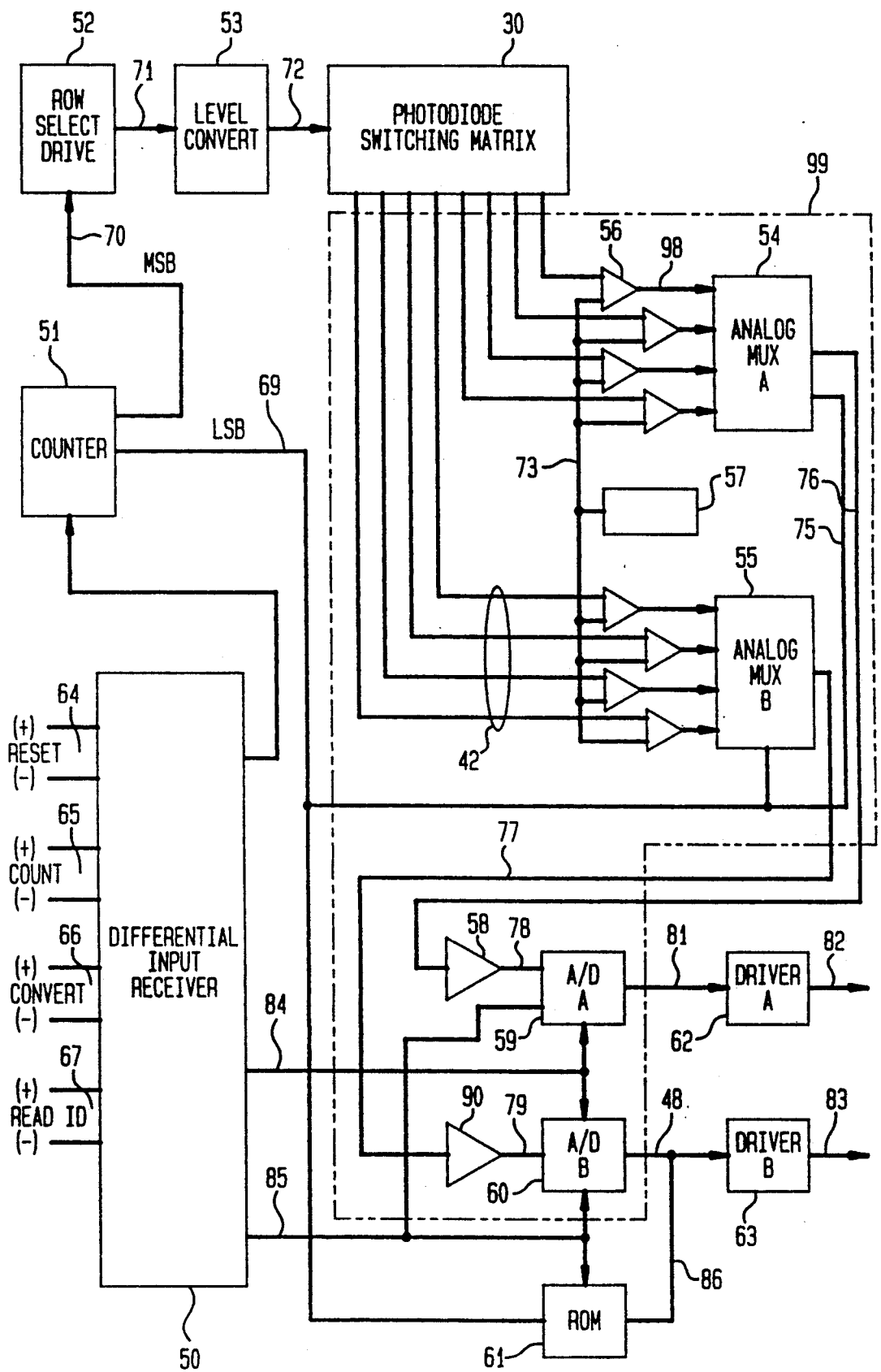
FIG. 4 is a schematic diagram of the detect head of the verifying and machining system of the present invention.

The system also includes verifier detect head 14. Referring now to FIG. 4, verifier detect head 14 includes means for detecting portions of the light source impinging on machined features of the verifying substrate 16, where the detecting means produces at least first and second sets of electrical signals. In the illustrated embodiment the detecting means comprises matrix 30 of photodiode switching circuits, each circuit having at least an input and an output and producing an output signal in response to the energy. The detecting means may be located on the opposite side of substrate 16 from light source 13, as shown in the figure, or may be located elsewhere, in which case the portions of the light impinging on the machined features may be directed to the detecting means by a suitable reflective device.

Figure 2:
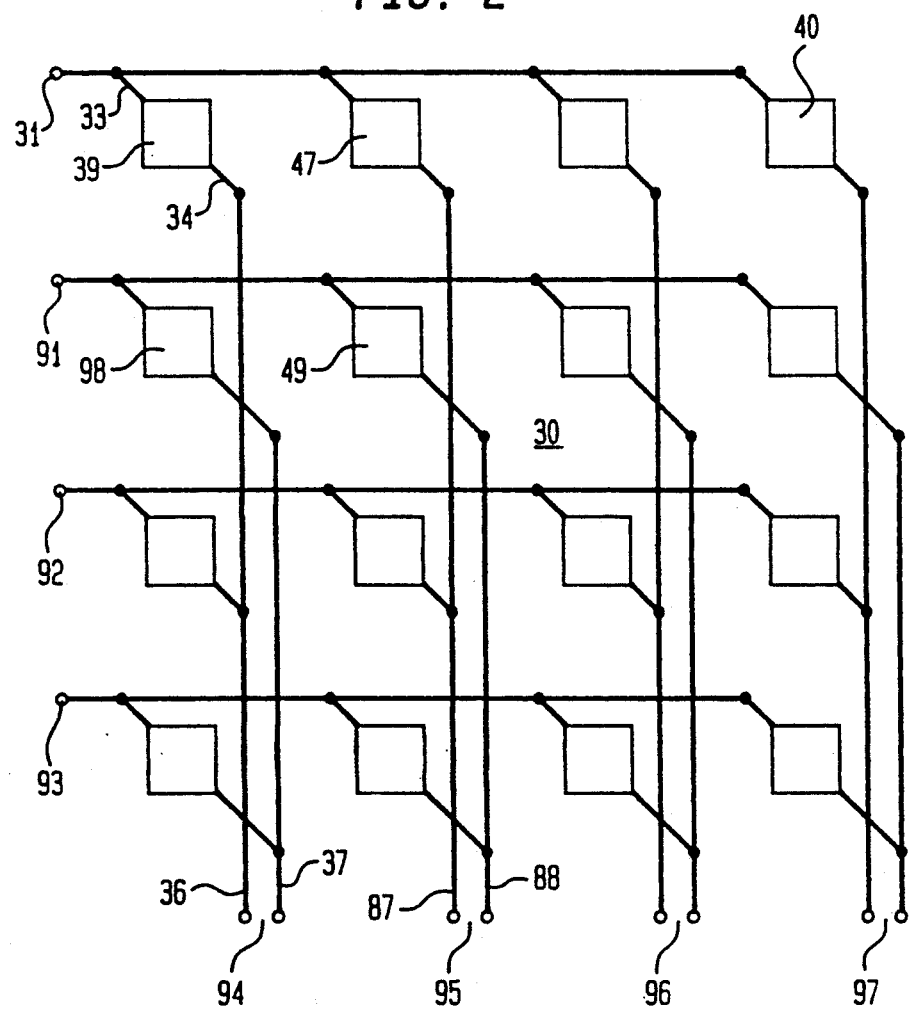
FIG. 2 is a schematic diagram of the photodiode switching circuit array of the present invention.

Referring now to FIG. 2, a preferred embodiment of matrix 30 is shown wherein the matrix 30 comprises a two dimensional matrix arranged in rows and columns with each switching circuit, such as circuit 40, having a row input 31 and a column output 97. In the illustrated embodiment the verifying substrate 16 is divided into a plurality of sectors and at least one switching circuit corresponds to at least one sector, preferably each switching circuit corresponding to each sector. Use of this configuration allows a verification of a machining operation in each sector of the entire substrate, without translating the substrate, in a manner which will be further described hereinafter. Each row has at least a single input and each column has at least two outputs. As can be seen from FIG. 2, in a preferred embodiment each row has one input and each column has two outputs.

Referring again to FIG. 4, the verifier detect head 14 further comprises means for converting the electrical signals into at least a first and second string of multiplexed digital output data. The converting means 99 includes at least one multiplexer and at least one analog to digital converter. In the illustrated embodiment the converting means comprises operational amplifiers 56, reference 57, analog mux A 54, analog mux B 55, amplifiers 58, 90, analog to digital converter A 59, and analog to digital converter B 60.

Referring again to FIG. 1, the system 21 also comprises verifier controller means 12 for comparing the digital output data with a predetermined set of data to determine accuracy of the machining operation. In a preferred embodiment verifier controller 12 includes memory means which contain calibration data for the photodiode switching circuits, the calibration data reflecting the values of the output for each switching circuit which represent a range of conditions of a machine feature. The digital signals representing the switching circuit outputs range from no output representing the complete absence of a hole to an output corresponding to a partially blocked hole to an output corresponding to a totally open hole and in a preferred embodiment these outputs are proportional to the condition of the hole. The function of verifier controller 12 will be further explained hereinafter.

The system 21, in a preferred embodiment, also includes means for machining substrate 15 in a machining position. The machining means 11 may include, but is not limited to, any of the methods described in the background of the invention, such as a multiple punch apparatus or laser drilling system. In the preferred embodiment the machining means 11 is a multiple punch apparatus such as described in Kranik, U.S. Pat. No. 4,425,829.

Referring again to FIG. 4, detect head 14 of the present invention also includes counter means 51 which provide a digital word composed of most significant bits on line 70 and of least significant bits on line 69. The most significant bits provide selecting signals to predetermined switching circuits and the least significant bits provide indicating signals to the converting means on lines 74 and 75 in a manner which will be further described hereinafter.

The digital output data on lines 81, 48 comprises an at least two bit digital word and in a preferred embodiment is an eight bit digital word. The use of an eight bit digital word to reflect the range of value of the output current of the photodiode allows a great degree of flexibility in system operation.

Referring again to FIG. 2, switching circuit matrix 30 of the present invention is shown. The embodiment illustrated in the Figure is a matrix comprising four rows and four columns. This simplified example is only for purposes of illustration and not for purposes of limitation. In an embodiment currently being used, matrix 30 comprises 16 rows and 16 columns and thus has 256 switching circuit elements. As previously stated each row has a single input and each column has two outputs. In the illustrated embodiment the first output of each column, for example output 36, corresponds to the switching circuits on first rows 31, 92 and the second output of each column, for example output 37, corresponds to the switching circuits on second rows 91, 93. In the illustrated embodiment the first rows 31, 92 and the second rows 91, 93 are alternate rows. As previously stated, the matrix produces at least first and second sets of electrical signals and the converting means 99 produces at least a first and second string of digital output data. The first set of electrical signals and the first string of digital output data corresponds to first column outputs and the second set of electrical signals and the second string of digital data corresponds to the second column outputs.

Figure 3:
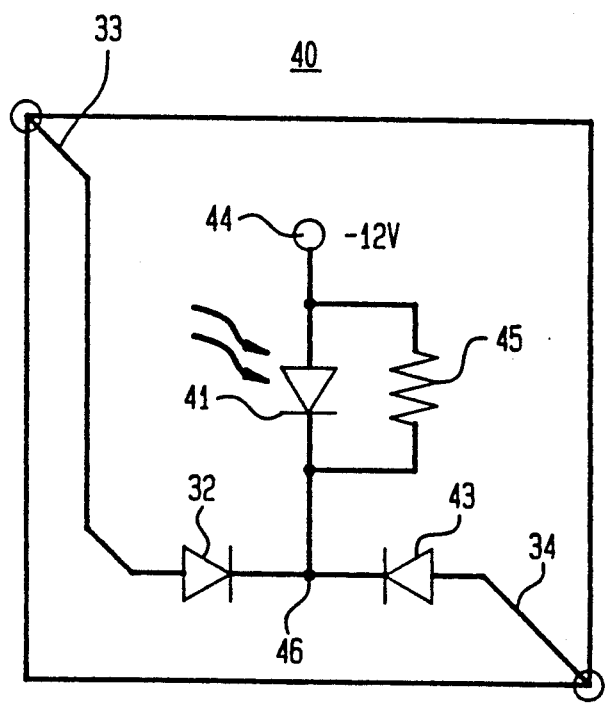
FIG. 3 is a schematic diagram of a photodiode switching circuit of the present invention.

Referring now to FIG. 3, photodiode switching circuit 40 of the present invention is shown. Circuit 40 includes photodiode 41 with its anode connected to voltage source 44. In the illustrated embodiment the voltage source is −12 volts and the photodiode is a Siemens part number BPX92 positive-intrinsic-negative (PIN) photodiode. Switching circuit 40 also includes input switching diode 32 with its anode connected to row input 33 of the circuit and its cathode connected to photodiode 41 cathode at point 46. Output switching diode 43 has its anode connected to column output 34 of circuit 40 and its cathode connected to the input diode and photodiode cathodes at point 46. Both the input and output switching diodes in the illustrated embodiment are type 1N4148 diodes. Current boost resistor 45 is connected in parallel with photo-diode 41. Current boost resistor 45 in the illustrated embodiment is a 1 M$\Omega$, 0.1%, metal film resistor.

Operation of the present invention with respect to the illustrated embodiment will now be described. When row input 33 is off it is at a voltage level of 0.6 volts and input diode 32 is forward biased. Since input diode 32 has a forward drop of approximately 0.6 volts, point 46 is at approximately zero volts in this condition. Column output 34 is always held at approximately zero volts, so in this condition any forward bias on output diode 43 is removed. With no forward bias output diode 43 acts like an open switch and photodiode 41 has no electrical connection to column output 34.

When row input 33 is selected, its voltage level is approximately −0.6 volts. Point 46 is also at approximately −0.6 volts and output diode 43 is forward biased. Photodiode current can pass through output diode 43 on column output 34 and the output of the switching circuit can be read. Since input diode 32 is no longer forward biased it acts like an open switch and can be ignored. Photodiode 41 produces current in response to light source 13 in the approximate range of 250 nA to 750 nA. Since the switching speed of output diode 43 is proportional to the conducted current it is desirable to increase this current level. This is accomplished by adding current boost resistor 45 in parallel with photodiode 41 to provide an additional current path. With the selected 1 M$\Omega$ resistor across a voltage drop of 12 volts a current of 12 micro amp flows, which when added to the photodiode current, increases output diode 43 switching time by an order of magnitude. Compensation for this additional current so that only the photodiode current is measured will be described hereinafter.

Before the verification system is operated, photodiode switching circuit matrix 30 must first be calibrated. During calibration detect head 14 is read several times as the light level of light source 13 is modulated by signals from verifier controller 12 over line 18. When all readings have been recorded threshold tables are created and stored in verifier controller 12. A threshold table entry contains a value or range of values corresponding to the readings for each photodiode circuit for particular hole conditions. Since all photodiode circuits respond differently the threshold table entries will vary, with compensation for different response levels. As previously described, a continuum of photodiode output currents will be produced, corresponding to the condition of a hole. The threshold value stored in the table corresponds to a hole which is sufficiently open to be suitable for product usage. Once this characterization is complete the light level will be set to the desired level for product type and hole diameter. Data corresponding to the hole locations for the verifying substrate 16 test is also stored in verifier controller 12.

Once calibration is complete, machining and verifying operations can be performed. Referring to FIG. 1, verifier controller 12 controls operation of the entire system. Verifier controller 12 interfaces with machining means 11 over line 17, with light source 13 over line 18, with verifier detect head 14 over line 19, and with X-Y table 10 over line 20. Verifier controller 12 is illustrated as a distinct device but may of course be made up of separate devices each of which performs one of the described functions.

In the preferred embodiment of the invention where a multiple punch apparatus is used, holes will be simultaneously punched for each of a plurality of chip sites on an electronics substrate. In the illustrated embodiment up to 1,000 holes will be punched on machining substrate 15, which is preferably an MLC green sheet, at each of 121 chip sites on an 11×11 array. Each of the chip sites corresponds to one of the previously described sectors of the photodiode matrix array. The entire machining operation is complete in from 12-50 sec., depending on the hole configuration of the substrate, with future increases in machining speed likely. As previously described, in the illustrated embodiment the photodiode matrix is a 16×16 matrix with a total of 256 photodiode switching circuits, thus allowing for considerable product expansion capability from the currently used 11×11 portion of the matrix corresponding to the substrate. The system of the present invention is also capable of verifying for more than 1,000 holes at each chip site. To verify simultaneously with operation of the multiple punch apparatus, the verifier detect head 14 and verifier controller 12 must sense and process the outputs of the entire photodiode switching circuit matrix in 1 msec.

The processing within verifier detect head 14 for each position of X-Y table 10 will now be described with reference to FIGS. 2 and 4. External control signals are received by differential input receiver 50. The inputs on lines 64, 65, 66, 67, as well as the verifier detect head outputs on lines 82, 83 correspond to line 19 in FIG. 1. The reset signal on line 64 initializes counter 51 over line 68. The count signal on line 65 initiates counter 51 over line 68 which produces signals corresponding to the addresses of each of the switching circuits in photodiode switching circuit matrix 30. The convert signal on line 66 is input to analog to digital converters A 59 and B 60 over line 84. The read ID signal on line 67 is input to ROM 61 and analog to digital converters A 59 and B 60 over line 85. Each of these input signals are converted to TTL levels in differential input receiver 50.

After initiation by the count signal, counter 51 sequentially generates a series of digital words, each digital word corresponding to the address of a photodiode circuit to be activated. The four most significant bits of the digital word are input to row select drive 52 over line 70 which generates a signal on line 71 for row selection. Level converter 53 converts this TTL level signal to a +/−0.6 volt level, which as previously described, is the operating voltage range for the input diode of the switching circuit. These levels are applied over lines 72 to two rows of switching circuits, resulting in an output for each of the switching circuits in these rows. The reason for activating two rows at a time will be further explained hereinafter. Switching matrix output lines 42 connect to operational amplifiers 56 which convert the output currents to voltages. The voltage of voltage reference 57 is input to operational amplifiers 56 over lines 73 so that the portion of the switching circuit output which is due to the current boost resistor current may be subtracted from the output. The operational amplifier 56 outputs on line 98 are inputs to analog mux A 54 and analog mux B 55. As previously described regarding FIG. 2, the simplified example in FIG. 4 illustrates eight matrix 30 outputs on lines 42 and eight amplifiers 56. A currently used embodiment has 32 outputs and 32 amplifiers for the 16×16 matrix.

The four least significant bits of the digital word from counter 51 on line 69 for each count are input to analog mux A 54 on line 75 and to analog mux B 55 on line 74. These signals indicate which of the inputs to the multiplexers on lines 98, i.e. which column outputs of matrix 30 should be multiplexed. For each set of most significant bits corresponding to a pair of rows, counter 51 will cycle through least significant bits until each column output for desired circuits in the designated row is input to the multiplexers. For each count corresponding to a switching circuit address there exists a unique set of most significant bits and a unique set of least significant bits.

Matrix 30 inputs on lines 31, 91, 92, and 93 in FIG. 2 correspond to the level covert 53 outputs on line 72 in FIG. 4 and matrix 30 outputs on lines 94, 95, 96, and 97 in FIG. 2 correspond to amplifier 56 inputs on lines 42 in FIG. 4. As previously described there are twice as many switching matrix 30 outputs as there are inputs. This enables two rows to be selected at a given time even though the switching circuits corresponding to only one row are read. This allows time for set up of switching circuits and corresponding amplifiers of one row while the switching circuit outputs of the other row are read. A 30 μsec. delay at the beginning of the cycle allows set up of the switching circuits and amplifiers of the first row.

For example, rows 31 and 91 are energized and a 30 μsec. delay time elapses. The switching circuits in row 31 are then read two at a time. The column outputs of circuits 39, 47 can be sampled on lines 36, 87, respectively and input to analog mux A 54 and B 55. As previously described, the least significant bits of counter 51 output on line 69 will dictate that these circuit outputs be read. The circuits in row 31 will be read in pairs until all desired circuits in the row are read.

The output of counter 51 on line 70 will then change most significant bits and select rows 91 and 92. The circuits in row 91 are already set up from the previous selection and the outputs of the pairs of switching circuits, e.g., the outputs of circuits 98, 49 on lines 37, 88 can be read while the circuits in row 92 settle. The entire matrix of switching circuits is sequentially activated and read in this manner to the extent required, the outputs providing first and second sets of electrical signals as the pairs of switching circuits are read. Detecting the outputs on the analog multiplexers thus comprises sequentially addressing the switching circuits such that the output of a first set of switching circuits is sensed while a second set of switching circuits is selected and settles, this sequential addressing proceeding until the outputs of all the desired switching circuits are sensed.

Stated differently, detecting the outputs of the circuits first comprises selecting two rows of switching circuits such as rows 31, 91. The outputs of sensing circuits in the first 31 of the two rows are sequentially sensed in pairs, 39 and 47, etc., until all desired circuits in the first row 31 are sensed. This procedure is repeated with sequentially selected pairs of rows until all desired circuits of the matrix 30 are sensed, with the first row of a newly selected pair of rows, such as 91, 92 being the second row of the pair of rows selected immediately previously, such as 31, 91. If the first row of the pair of rows is the first row of the detecting sequence, sensing the output of the switching circuits in that row is delayed to allow the switching circuits and amplifiers to settle.

The outputs of analog mux A 54 and analog mux B 55 on lines 76, and 77, respectively, thus provide a sequential multiplexed analog signal consisting of the photodiode switching circuit outputs. These signals are amplified by amplifiers 58, 90 and input to analog to digital converter A 59 and analog to digital converter B 60 over lines 78 and 79 respectively. The analog signals are then digitized to 8 bit resolution in response to the convert commands over line 84. The digitized signals are input to driver A 62 and driver B 63 on lines 81, 48, respectively, which in turn send these signals to verifier controller 12 over lines 82 and 83 respectively, which as previously described correspond to line 19 in FIG. 1. After all 256 switching circuits are sensed and compared with the stored hole location data and threshold values in verifier controller 12, the X-Y table translates machining substrate 15 and verifying substrate 16 to a new position and the entire procedure is repeated for the next set of holes. This process continues until the machining of the entire substrate is verified, which is simultaneous with the completion of machining of machining substrate 15.

ROM 61 is programmed with identification data pertinent to a predetermined detect head over line 85. This data may be read by the verifier controller in response to the read ID command on lines 67, 85. The correct ROM address is indexed in response to the least significant bits on line 69 and the ROM's output is read by verifier controller 12 over lines 86 through driver B 63 and line 83, while the outputs of analog to digital converters A 59 and B 60 are disabled by the read ID signal on line 85.

While the invention has been illustrated and described with reference to preferred embodiments thereof, it is to be understood that the invention is not limited to the precise construction herein disclosed and the right is reserved to all changes and modifications coming within the scope of the invention as defined in the appended claims.

What is claimed is:

1. A system for verifying substrate machining, comprising:
   means for mounting a substrate;
   an energy beam source located to impinge upon the substrate;
   means for detecting portions of the energy beam impinging on machined features of the substrate, the detecting means comprising a matrix of switching circuits, each switching circuit corresponding to a respective machined feature of substrate, and each switching circuit being responsive to the portion of the energy beam impinging on the respective machined feature for developing an electrical signal characterizing the respective machined feature, wherein the matrix is arranged in rows and columns, wherein the switching circuits have row inputs and column outputs, and wherein each row has at least a single input and each column has at lest two outputs;
   means for converting each electrical signal into a string of digital output data; and
   verifier controller means for comparing the digital output data with a predetermined set of data to verify machining accuracy.

2. The system of claim 1 wherein the energy beam source comprises an electromagnetic energy source.

3. The system of claim 2 wherein the electromagnetic source comprises a light source.

4. The system of claim 3 wherein the light source is a visible light source.

5. The system of claim 1 wherein the matrix is a two dimensional matrix.

6. The system of claim 5 wherein the matrix is arranged in rows and columns and wherein each switching circuit has a row input and a column output.

7. The system of claim 1 wherein the substrate is divided into a plurality of sectors and at least one switching circuit corresponds to each of the sectors.

8. The system of claim 1 wherein the substrate is divided into a plurality of sectors and each switching circuit corresponds to at least one of the sectors.

9. The system of claim 1 further comprising counter means for providing selecting signals to predetermined switching circuits and for providing signals to the converting means, the signals indicating predetermined switching circuit outputs to be converted.

10. The system of claim 9 wherein the counter means provides a digital word composed of most significant bits and least significant bits, the most significant bits providing the selecting signals to the predetermined switching circuits and the least significant bits providing the indicating signals to the converting means.

11. The system of claim 1 wherein the digital output data comprises an at least two bit digital word.

12. The system of claim 11 where the value of the digital word represents the condition of a machined feature under verification.

13. The system of claim 12 wherein the verifier controller means includes memory means containing calibration data for the switching circuits, the calibration data reflecting the values of the output for each switching circuit which represent a range of conditions of a machined feature.

14. The system of claim 1 further comprising counter means for providing selecting signals to predetermined switching circuits and for providing signals to the converting means, the signals indicating predetermined switching circuit outputs to be converted.

15. The system of claim 14 wherein the first output of each column corresponds to switching circuits on first rows and the second output of each column corresponds to switching circuits on second rows.

16. The system of claim 15 wherein the first rows and second rows are alternate rows.

17. The system of claim 1 further comprising means for translating the substrate.

18. The system of claim 17 wherein the translating means further comprises means for mounting a substrate to be machined.

19. The system of claim 18 further comprising means for machining the substrate.

20. The system of claim 1 wherein the converting means comprises at lest one multiplexer and at least one analog to digital converter.

21. A substrate machining system, comprising:
    means for mounting a verifying substrate;

an electromagnetic energy source placed to impinge upon the verifying substrate;

a two-dimensional matrix of photodiode switching circuits placed to detect energy impinging on machined features of the verifying substrate, each circuit corresponding to a respective machined feature of the verifying substrate, and each circuit being responsive to the energy impinging on the respective machined feature for developing an output signal characterizing the respective machined feature, wherein the matrix is arranged in rows and columns, wherein each circuit is operative to produce an output signal in responsive to light, wherein the circuits have row inputs and column outputs, and wherein each row has at least a single input and each column has at least two outputs;

means for converting the switching circuit output signals into multiplexed digital output data; and verifier controller means for comparing the digital output data with a predetermined set of data to verify machining accuracy.

22. The system of claim 21 wherein the matrix switching circuit outputs comprise at least first and second strings of electrical signals and the multiplexed digital output data comprises at least a first and second string of digital output data.

23. The system of claim 22 wherein the electromagnetic energy source comprises a light source.

24. The system of claim 21 further comprising:
means for mounting a machining substrate;
means for translating both the machining substrate and the verifying substrate; and
means for machining the machining substrate.

25. The system of claim 21 further comprising counter means for providing selecting signals to predetermined switching circuits and for providing signals to the converting means, the signals indicating predetermined switching circuit outputs to be converted.

26. The system of claim 25 wherein the counter means provide a digital word composed of most significant bits and least significant bits, the most significant bits providing the selecting signals to the predetermined switching circuits and the least significant bits providing the indicating signals to the converting means.

27. The system of claim 21 wherein the substrate is divided into a plurality of sectors and at least one switching circuit corresponds to at least one of the sectors.

28. The system of claim 21 wherein the digital output data comprises an at least two bit digital word.

29. The system of claim 28 wherein the value of the digital word represents the condition of a machined feature under verification.

30. The system of claim 29 wherein the verifier controller means includes memory means containing calibration data for the switching circuits, the calibration data reflecting the values of the output for each switching circuit which represent a range of conditions of a machined feature.

31. The system of claim 21 wherein the first output of each column corresponds to switching circuits on first rows and the second output of each column corresponds to switching circuits on second rows.

32. The system of claim 31 wherein the first set of electrical signals and the first string of output data corresponds to the first column outputs and the second set of electrical signals and the second string of digital data corresponds to the second column outputs.

33. The system of claim 31 wherein the first row and second rows are alternate rows.

34. The system of claim 21 wherein the converting means comprises at least one multiplexer and at least one analog to digital converter.

35. A method for verifying substrate machining, comprising the steps of:
mounting a substrate;
locating an energy beam for impinging on the machined features of the substrate;
detecting portions of the energy beam impinging on machined features of the substrate using a matrix of photodiode switching circuits, each circuit having at least an input and an output, and said matrix responsively producing at least two sets of electrical signals, each signal corresponding to a respective machine feature of the substrate, and each signal characterizing the respective machined feature, wherein the matrix is arranged in rows and columns, wherein each switching circuit has a row input and column output and wherein each row has a single input and each column has at least two outputs;
converting each electrical signal into a string of digital output data; and
comparing the digital output data with a predetermined set of data to verify machining accuracy.

36. The method of claim 35 wherein the energy beam comprises an electromagnetic beam.

37. The method of claim 35 wherein the detecting step comprises sequentially sensing the output of each photodiode switching circuit and wherein the substrate is divided into a plurality of sectors and at least one switching circuit corresponds to at least one sector.

38. The method of claim 35 further comprising selecting predetermined switching circuits with output of a counter.

39. The method of claim 38 further comprising providing signals from the counter output to indicate predetermined switching circuit outputs for converting the switching circuit outputs to digital output data.

40. The method of claim 39 wherein the counter output is a digital word composed of most significant bits and least significant bits and the providing step comprises supplying the least significant bits of the counter output to indicate the predetermined switching circuit outputs.

41. The method of claim 38 wherein the counter output is a digital word composed of most significant bits and least significant bits and the selecting step comprises supplying the most significant bits of the counter output to the switching circuit matrix.

42. The method of claim 35 wherein the switching circuits outputs are digital words and further comprising calibrating the switching circuit outputs to generate the predetermined set of data.

43. The method of claim 42 wherein the calibrating comprises establishing data values for each switching circuit which correspond to the condition of a machined feature.

44. The method of claim 35 wherein the converting step further comprises multiplexing the electrical signals.

45. The method of claim 35 wherein the detecting step comprises:
a) selecting two rows of switching circuits;

b) sequentially sensing the outputs of pairs of circuits in the first of the two rows until all desired circuits in the first of the two rows are sensed; and c) sequentially selecting pairs of rows and repeating steps a) and b) until all desired circuits are sensed, wherein the first row of the sequentially selected pair is the second of the two rows in step b; wherein a delay in the sensing in step b) sufficient to allow sensing circuit settling is imposed if the first of the two rows is the first row of the detecting step.

46. The method of claim 35 wherein the detecting step comprises sequentially addressing the switching circuits such that the output of a first set of switching circuits is sensed while a second set of switching circuits is selected and settles, the sequential addressing proceeding until the outputs of all desired switching circuits are sensed.

47. A method for machining substrates, comprising the steps of:

mounting a substrate in a machining position;
machining desired features in the substrate;
translating the substrate to a verifying position;
locating an energy beam for impinging on the machined features of the substrate;
selecting predetermined switching circuits;
detecting portions of the energy beam impinging on machined features of the substrate with an array of photodiode switching circuits, each switching circuit having at least an input and an output, and said array responsively producing at least two sets of output signals, each output signal corresponding to a respective machined feature of the substrate, and each output signal characterizing the respective machined feature, wherein the array is arranged in rows and columns, wherein each switching circuit has a row input and a column output and wherein each row has a single input and each column has at least two outputs;
providing electrical signals to indicate predetermined switching circuit inputs;
converting the electrical signals into digital output data; and
comparing the digital output data with a predetermined set of data to verify machining accuracy.

48. The method of claim 47 wherein the machining comprises drilling holes.

49. The method of claim 47 further comprising mounting an unmachined substrate in the machining position after translating the machined substrate to the verifying position.

* * * * *